(12) United States Patent
Tass

(10) Patent No.: US 9,592,384 B2
(45) Date of Patent: Mar. 14, 2017

(54) METHOD FOR THE DESYNCHRONIZATION OF NEURAL BRAIN ACTIVITY

(71) Applicant: Forschungszentrum Juelich GmbH, Juelich (DE)

(72) Inventor: Peter A. Tass, Munich (DE)

(73) Assignee: Forschungszentrum Jülich GmbH, Jülich (DE)

( * ) Notice: Subject to any disclaimer, the term of this patent is extended or adjusted under 35 U.S.C. 154(b) by 0 days.

(21) Appl. No.: 14/996,578

(22) Filed: Jan. 15, 2016

(65) Prior Publication Data

US 2016/0243364 A1    Aug. 25, 2016

Related U.S. Application Data

(60) Division of application No. 13/887,713, filed on May 6, 2013, now abandoned, which is a division of
(Continued)

(30) Foreign Application Priority Data

Apr. 17, 2003 (DE) .................................. 103 18 071

(51) Int. Cl.
*A61N 1/36* (2006.01)

(52) U.S. Cl.
CPC ..... *A61N 1/36064* (2013.01); *A61N 1/36017* (2013.01); *A61N 1/36067* (2013.01); *A61N 1/36082* (2013.01); *A61N 1/36135* (2013.01)

(58) Field of Classification Search
CPC .............. A61N 1/3606; A61N 1/36064; A61N 1/36067; A61N 1/36082; A61N 1/36085;
(Continued)

(56) References Cited

U.S. PATENT DOCUMENTS

| 5,299,569 A | 4/1994 | Wernicke et al. |
| 5,540,734 A | 7/1996 | Zabara |

(Continued)

FOREIGN PATENT DOCUMENTS

| EP | 1 145 736 A2 | 10/2001 |
| WO | WO-97/42990 A1 | 11/1997 |
| WO | WO-01/93953 A1 | 12/2001 |

OTHER PUBLICATIONS

Paydarfar, D. et al.; "Phase resetting and dysrhythmic responses of the respiratory oscillator", The American Physiological Society. 252, 1987. pp. 55-62.
(Continued)

*Primary Examiner* — George Evanisko
(74) *Attorney, Agent, or Firm* — Arent Fox LLP

(57) ABSTRACT

A method is disclosed for desynchronizing neuronal brain activity of a patient in which the brain activity involves a neuron population firing in a synchronized manner. The method includes measuring a pathological frequency g of the neuronal brain activity of the patient, where the pathological frequency g relates to a pathological disorder of the patient. The method further includes calculating a stimuli frequency f based on the measured pathological frequency g, where the stimuli frequency f is calculated as being equal to the measured pathological frequency g×n/m, where n is 1, 2 or 3 and m is 1, 2 or 3, and controlling an electrode to generate stimuli in sequence with the stimuli succeeding each other at the stimuli frequency f, where the stimuli stimulate the neuron population of the patient.

9 Claims, 5 Drawing Sheets

Related U.S. Application Data application No. 13/028,923, filed on Feb. 16, 2011, now Pat. No. 8,463,386, which is a continuation of application No. 10/553,679, filed as application No. PCT/DE2004/000737 on Apr. 8, 2004, now Pat. No. 7,917,221.

(58) Field of Classification Search
CPC ............ A61N 1/36089; A61N 1/36092; A61N 1/36096; A61N 1/36103
See application file for complete search history.

(56) References Cited

U.S. PATENT DOCUMENTS

| | | | |
|---|---|---|---|
| 5,938,688 A | 8/1999 | Schiff | |
| 5,978,702 A | 11/1999 | Ward et al. | |
| 6,459,936 B2* | 10/2002 | Fischell | A61N 1/36017 607/45 |
| 6,466,822 B1 | 10/2002 | Pless | |
| 6,529,774 B1 | 3/2003 | Greene | |
| 6,944,501 B1 | 9/2005 | Pless | |
| 7,174,213 B2 | 2/2007 | Pless | |
| 2001/0051819 A1 | 12/2001 | Fischell et al. | |
| 2002/0072770 A1 | 6/2002 | Pless | |
| 2002/0077670 A1 | 6/2002 | Archer et al. | |
| 2005/0125043 A1 | 6/2005 | Tass | |

OTHER PUBLICATIONS

Leznik, E. et al.; "Electrotonically Mediated Oscillatory Patterns in Neuronal Ensembles: An in Vitro Voltage-Dependent Dye-Imaging Study in the Inferior Olive"; The Journal of Neuroscience, Apr. 1, 2002, 22(7), pp. 2804-2815.

Jackson, A. et al.; "Rhythm generation in monkey motor cortex explored using pyramidal tract stimulation", Journal of Physiology (2002, 541.3, pp. 685-699.

Tass, P. et al.; "Obsessive-Compulsive Disorder: Development of Demand-Controlled Deep Brain Stimulation with Methods from Stochastic Phase Resetting", Neuropsychopharmacology (2003) 28, pp. S27-S34.

Tass, P; "Effective desynchronization with bipolar double-pulse stimulation", Physical Review E 66, 2002.

Tass, P.; "Stochastic phase rsetting of stimulus-locked responses of two coupled oscillators: Transient response clustering, synchronization, and desynchronization"; Chaos, vol. 3, No. 1, Mar. 2003, pp. 364-376.

Tass, P. et al.; "Detection of n:m Phase Locking from Noisy Data: Application to Magnetoencephalography"; Physical Review Letters, vol. 81, No. 15, Oct. 12, 1998, pp. 3291-3294.

Tass, P.; "Effective desynchronization by means of double-pulse phase resetting"; Europhysics Letters, 53(1), Jan. 1, 2001, pp. 15-21.

Tass, P.; "Effective desynchronization with a resetting pulse train followed by a single pulse"; Europhysics Letters, 55 (2), Jul. 15, 2001, pp. 177-177.

Tass, P.; "Effective desynchronization with a stimulation technique based on soft phase resetting"; Europhysics Letters, 57 (2), Jan. 15, 2002, pp. 164-170.

Tass, P.; "Desynchronization of brain rhythms with soft phase-resetting techniques"; Biological Cybernetics, 87, 2002, pp. 102-115.

Deetjen and Speckmann; "Physiologie". © 1999 Urban & Fischer Verlag, Muenchen, Stuttgart, Jena, Luebeck, Ulm (p. 11, left column, paragraph 2, meaning of the term depolarization—means reduction of the membrane potential below the value of the equilibrium rest membrane potential).

Tass, Peter A; "Desynchronizing double-pulse phase resetting and application to deep brain stimulation"; Biological Cybernetics, 85, pp. 343-354, 2001.

Levy, Ron et al.; "High-frequency Synchronization of Neuronal Activity in the Subthalamic Nucleus of Parkinsonian Patients with Limb Terryr"; The Journal of Neuroscience, Oct. 15, 2000, 20(20), pp. 7768-7775.

Best, E.N.; "Null Space in the Hodgkin-Huxley Equations—A Critical Test": Biophys. J. © Biophysical Society, vol. 27, Jul. 1979, pp. 87-104.

Demir, S.S. et al.; "Phase Sensitivity and Entrainment in a Modeled Bursting Neuron"; Biophysical Journal, vol. 72, Feb. 1997, pp. 579-594.

Best, E.N.; "Null Space in the Hodgkin-Huxley Equations—A Critical Test": Biophys. J. © Biophysical Society, vol. 27, Jul. 1979, 87-104.

Perkel, D.H, et al.; "Pacemaker Neurons Effects of Regularly Spaced Synaptic Input"; Science, vol. 145, Jul. 3, 1964, pp. 61-63.

Nini, A. et al; "Neurons in the Globus Pallidus Do Not Show Correlated Activity in the Normal Monkey, but Phase-Locked Oscillations Appear in the MPTP Model of Parkinsonism"; Journal of Neurophysiology, vol. 74, No. 4, Oct. 1995, pp. 1800-1805.

Pinsker, H.; "Aplysia Bursting Neurons as Endogenous Oscillators. I. Phase-Response Curves for Pulsed Inhibitory Synaptic Input", Journal of Neurophysiology, vol. 40, No. 3, May 1977, pp. 527-543.

Brown, P, et al; What do the basal ganglia do?; The Lancet, vol. 351, Jun. 13, 1998, pp. 1801-1804.

Brown, P, MD; "Oscillatory Nature of Human Basal Ganglia Activity: Relationship to the Pathophysiology of Parkinson's Disease"; Movement Disorders, vol. 18, No. 4, 2003, pp. 357-363.

Brown, P., et al;"Dopamine Dependency of Oscillations between Subthalamic Nucleus and Pallidum in Parkinson's Disease"; The Journal of Neuroscience, Feb. 1, 2001, vol. 21, No. 3, pp. 1033-1038.

Hämäläinen, Matti et al; "Magnetoencephalography—theory, instrumentation, and applications to noninvasive studies of the working human brian"; Reviews of Modern Physics, vol. 65, No. 2, Apr. 1993, pp. 413-497.

Volkmann, Jens, MD et a.; "Introduction to the Programming of Deep Brain Stimulators"; Movement Disorders vol. 17, Suppl.3, 2002. pp. S181-S187.

Titcombe, Michele S. et al.; "Dynamics of Parkinsonian tremor during deep brain stimulation"; Chaos. vol. 11, No. 4, Dec. 2001, pp. 766-773.

Dostrovsky, Jonathon O., et al; "Mechanisms of Deep Brain Stimulation"; Movemement Disorders, vol. 17, Suppl. 2, 2002, pp. S63-S68.

Warman E., et al.; "Desynchronization of Epileptiform Activity by Phase Resetting": IEEE Engineering in Medicine & Biology Society. 11$^{th}$ Annual International Conference, 1989, pp. 1286-1287.

Durand, Dominique M. et al; "Desynchronization of epileptiform activity by extracellular current pulses in rat hippocampal slices"; Journal of Physiology 480.3, 1994, pp. 527-537.

* cited by examiner

METHOD FOR THE DESYNCHRONIZATION OF NEURAL BRAIN ACTIVITY

CROSS REFERENCE TO RELATED APPLICATIONS

This application is a divisional application of U.S. patent application Ser. No. 13/887,713, filed on May 6, 2013, which is a divisional application of U.S. patent application Ser. No. 13/028,923, filed on Feb. 16, 2011, now U.S. Pat. No. 8,463,386, which is a continuation of U.S. patent application Ser. No. 10/553,679, filed on Oct. 17, 2005, now U.S. Pat. No. 7,917,221, which is the National Stage of PCT No. PCT/DE04/00737, filed on Apr. 8, 2004, which claims the benefit of German Application No. 103 18 071.0, filed on Apr. 17, 2003, all of which are incorporated by reference herein.

TECHNICAL FIELD

The invention relates to a device for the desynchronization of neuronal brain activity in accordance with the preamble of claim 1.

BACKGROUND OF THE INVENTION

In patients with neurological or psychiatric disorders, for example Parkinsonism (Morbus Parkinson), essential tremor, dystony or obsessive disorders, nerve cell groups or networks in circumscribed regions of the brain, for example the thalamus and the basal ganglia, become pathologically active, for example, excessively synchronous in their activity. In this case a large number of neurons generate action potentials synchronously. The neurons involved fire predominantly synchronously. With healthy individuals, by contrast, the neurons in these regions of the brains fire qualitatively differently, for example in an uncontrolled manner.

In the case of Morbus Parkinson, the pathological synchronous activity for example of the thalamus and the basal ganglia, alter the neuronal activity in other grain regions, for example in areas of the cerebral cortex like the primary motor cortex. In that case, the pathological synchronous activity in the region of the thalamus and the basal ganglia has its rhythm impressed upon the cerebral cortex so that the muscles controlled by this region undergo pathological activity, for example, a rhythmic trembling (tremor).

In patients who no longer can be effectively treated by medication, depending upon the pathological patterns and whether the pathology arises from one side or both sides of the brain, a deep electrode can be implanted on one or both sides. A cable runs under the skin from the head to a so-called generator which comprises a control device and a battery and for example can be implanted under the skin in the region of the clavicle. Through the deep electrodes a continuous stimulation is applied with a high frequency periodic pulse sequence (pulse train with a frequency of >100 Hz) of individual pulses, for example rectangular pulses. The goal of this method is to suppress the firing of the neurons in the target regions. The mechanism by which this operates in standard stimulation has not been sufficiently clarified as yet. The results of multiple studies suggest that the standard deep stimulation operates like a reversible leisioning, that is a reversible switch off of the tissue: the standard deep stimulation suppresses the firing of the neurons in the target regions and/or in the brain regions connected therewith.

A disadvantage with this manner of stimulation is that the energy consumption of the generator is very high so that the generator, including its batteries must be replaced by an operative procedure relatively early, after about one to three years. Of even greater drawback is that the high frequency continuous stimulation is unphysiological (unnatural) input in the region of the brain for example the thalamus or the basal ganglia which in a few years can give rise to adaptation of the impacted nerve [c4ell] [cell] networks. In order to produce the same stimulation results, therefore, to overcome this adaptation, higher stimulation amplitudes must be used. The greater the stimulation amplitude, the greater is the probability that as a consequence and stimulation, neighboring areas will be subjected to collateral effects or damage like dysarthria (speech disturbances), dysaesthesis (in part from painful missynesthesia), cerebral ataxy (instability, inability to stand without assistance) or schizophrenic like symptoms, etc. These side effects cannot be tolerated by patients. The treatment, therefore loses its effectiveness in these cases after several years.

As a consequence, another method has been proposed as is described in the German Patent Document DE 102 11766.7 "Device for the Treatment of Patients by Means of Brain Stimulation, An Electronic Unit As Well As The Use of the Device and the Electronic Unit in Medicine", in which the demand-controlled excitation is applied to, respective target regions in which pathologically synchronized numonal activity is to be desynchronized. The goal of this method/this device is not simply to suppress the pathologically synchronous firing as with standard deep stimulation but to approximate the physiological uncorrelated firing patterns.

In this manner on the one hand the current consumption can be reduced and on the other hand, adaptation processes of the nerve tissue which can require an increase in the stimulation amplitude and give rise to side effects, can be prevented. This demand controlled desynchronization method has however also relevant drawbacks.

Drawbacks of the demand-controlled or need-controlled desynchronization stimulation method of DE 102 117 66.7 results from the following considerations:

In order to desynchronize a synchronized nerve cell network with an electric stimulus, an electrical stimulus of a certain duration must be applied at a certain phase of the pathological rhythmic activity in the target area with precision. Since such a precision cannot be readily determined experimentally at the present time, combinations of stimuli are used. A first stimulus or excitation pulse of such a composite stimulus controls the dynamics of the population to be desynchronized by a reset, that is a new start, while the second excitation of the composite stimulus encounters and desynchronizes the nerve cell group in a vulnerable state it is however unavoidable in this connection, to ensure that the quality of the control, that is the quality of the reset, to provide a stronger stimulus for the reset. This should however be avoided in the sense of minimizing side effects. It is decisive to this end that the desired desynchronizing effect can only arise when the stimulation parameters, thus the duration of the individual excitations and especially the pause between the first and second excitations are optimally selected. This has severe consequences:

1. A time consuming calibration procedure is required which typically lasts longer than 30 minutes
2. As a consequence of the time consuming calibration procedure, the effect of desynchronizing simulation in accordance with DE 102 117 66.7 cannot be made part of an intraoperative selection of the appropriate target point for the insertion of the deep electrode. For that purpose the effect of the desynchronization stimulation according to DE 102 117.66.7 must be tested separately for different target points since for each target point a separate calibration is required. This would decrease the duration of electrode implantation surgery for a patient in a prohibitive manner.

3. With large variations in the network characteristics, that is fluctuations in the parameters which describe the activity of the nerve cell population like, for example, synaptic amplitude and firing rate, new calibrations are required which means that during the calibration, no therapeutic effect can be produced.

4. Since the desynchronizing stimulation according to DE 102 66.7 can only be effective when the frequency of the neuron population to be desynchronized does not have large fluctuations, this stimulation cannot be used with pathologies in which the pathologically excessively synchronized activity arises for only brief periods of time and then with strongly varying frequencies as for example in the case of epilepsy.

SUMMARY OF THE INVENTION

It is, therefore, the object of the invention to provide a device for the desynchronization of neuronal brain activity with which the adaptation to a nonphysiological continuous stimulation can be suppressed in the treatment of patients with electrode stimulation. It should eliminate the need for lengthy and wearing calibration procedures and permit the stimulation even in the case when the main frequency components of the pathologically rhythmic activity is subject to large fluctuations. The stimulation device according to the invention should function in an electric power conserving manner so that the batteries implanted in the patient seldom require operative replacement.

Starting from the preamble of claim 1, the objects are achieved according to the invention by the features given in the characterizing part of claim 1. Surprisingly, the objects are achieved in that at least two partial regions of a brain area or at least two functionally associated brain areas are each respectively reset in their activity with at least two electrodes, that is reset with respect to other phases, whereby for an ill person surprisingly a desynchronization is found in the relevant neuron populations and the illness symptomatically suppressed.

With the device according to the invention it is thus possible immediately and directly to treat patients by means of a multielectrode stimulation, (I) without thereby an adaptation arising to a nonphysiological continuous stimulation, (ii) without the need for a lengthy and wearing calibration procedure, (iii) and even when the main frequency components of the pathological rhythmic activity are subjected to strong fluctuations.

As a consequence, the above mentioned side effects can be reduced or suppressed. The device according to the invention enables the effect of the desynchronization stimulation intra operatively applied by selection of the most suitable target point for the deep electrode, to be utilized for this purpose, during the implantation of the deep electrode in the region of the anatomically precalculated target point, the device according to the invention applies test stimuli as the deep electrode is moved in millimeter steps. The target point at which the best therapeutic effect will be produced in this test stimulation mode is selected as the target point for the permanent implantation. In addition, apart from the aforementioned illnesses which are associated mainly with pathologically synchronized activity with relatively constant frequencies, illnesses can be treated with which only intermittent (briefly arising) pathologically synchronous activity is associated. A main indication is therefore the treatment of epileptics who can no longer be treated by medication. The device of the invention can be used for example for illnesses like Morbus Parkinson, essential tremor, dystony, epilepsy and obsessive disorders where a desynchronization may be of interest.

The device of the invention operates in an electric current conserving manner so that the batteries implanted in the patient seldom require replacement.

Advantageous features of the invention are given in the dependent claims.

BRIEF DESCRIPTION OF THE DRAWINGS

The figures show exemplary embodiments of the invention.

They show.

DETAILED DESCRIPTION OF THE EXEMPLARY EMBODIMENT

Figure 1:
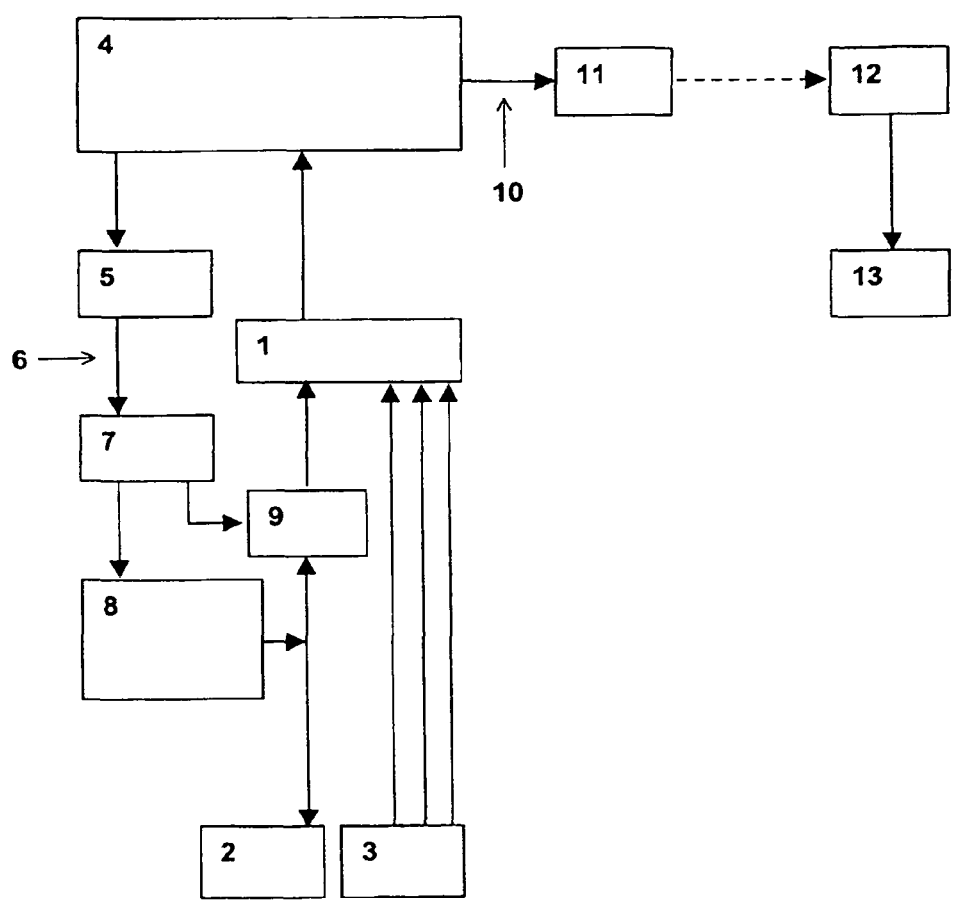
FIG. 1 illustrates a device according to the invention.

The device according to FIG. 1 comprises an isolating amplifier 1 connected to at least two electrodes 2 and sensors 3 for detecting the physiological measurement signals. The isolating amplifier is also connected with a unit for signal processing and control which is connected to an optical transmitter for the simulation 5. The optical transmitter 5 is connected by a light waveguide or conductor 6 with an optical receiver 7 which in turn is connected with a stimulator unit 8 for stimulation. The stimulator unit 8 for stimulation is connected with at least two electrodes. At the inlet region, to the isolating amplifier 1 at which the electrodes 2 are connected, there is a relay 9 or a transistor. The unit 4 is connected via a line 10 with a telemetry transmitter 11 which communicates with a telemetry receiver 12 located externally of the device to be implanted and providing means for visualizing, for processing and for storing the data 13. As sensors 3, for example, epicordical electrodes, deep electrodes, brain electrodes or peripheral electrodes can, for example, be used.

The electrodes 2 each respectively has at least two wires at whose ends a potential difference is applied for the purpose of stimulation. The electrodes can also be microelectrodes or macroelectrodes. Alternatively, the electrodes each can comprise a single wire. In this case for the purpose of the stimulation, respective potential differences are applied between the individual wire and the metallic part of the housing of the generator. Additionally but not obligatory, a potential difference can be measured by means of the electrodes in order to establish a pathological activity. In a further embodiment, the electrodes 2 can each also be comprised of more than two individual wires which can serve both for the determination of measurement signals in the brain as well as for the stimulation. For example, four wires can be provided in a conductor cable, whereby between different ends a potential difference can be applied or can be measured. In this manner the magnitude of the area of the brain from which the signal is derived as well as the area of the brain which is stimulated or the target area can be varied. The number of wires from which the electrodes are made is limited as to its upper value only by the maximum thickness of the cable which is to be inserted into the brain so that the smallest amount of brain matter will be damaged. Commercial electrodes comprise four wires, although five, six, or more wires or only two wires may be comprised in the electrode.

For the case in which the electrodes 2 each comprise more than two wires, at least two of these wires can also function as the sensors 3 so that in this special case an embodiment is provided in which the electrodes 2 and the sensors 3 can be united in a single component. The wires of the electrodes 2 can have different lengths so that they can penetrate to different depths in the brain. If the electrode 2 is comprised of n wires, a stimulation can be effected over at least one pair of wires so that by the pair formation subcombinations of wires are possible. Apart from this component additional sensors 3 can be provided which are not structurally united with the electrodes 2.

According to the invention, the device is provided with means which can recognize the signals from the electrodes 2 or the sensors 3 as pathological and in the case of a pathological pattern, limit through the electrodes to stimuli which act upon the pathological neuronal activity so that in the subpopulations of neurons which are stimulated by the individual electrodes, a reset occurs and the neuronal activity of the entire population is desynchronized and the natural physiological activity thus more closely approximated. The physiological activity from the healthy activity by a characteristic change in its patterns and/or its amplitude and/or its frequency count.

The means for reorganizing the pathological pattern can comprise a computer which processes the electrical signals from the electrodes 2 and/or the sensors 3 and compares the process signal with data stored in the computer. The computer makes available through a data carrier the data which is stored thereon. This can be enabled in the framework of a calibration and/or a control operation represented at 5.

The device according to the invention also comprises in one possible embodiment, a unit 4 for signal processing and/or control or regulation of a computer and which includes a data carrier which carries the data relating to pathological patrons and which can be compared with the measured data. When reference is made herein to the data of the pathological patterns, parameters and measurement values which are relevant for the stimulation are to be understood, for example, the instantaneous frequency of feedback signals measured by the sensor 3, the thresholds required for demand or need controlled timing, the stimulation parameters which determine the stimulation amplitude like for example the amplitude number of individual pulses of a high frequency pulse train. All of the process-wise relevant parameters which the device of the invention requires to determine the type and strength of the stimuli as well as the spacing in time thereof, and information pertinent to the electrode-specific applications of the stimuli which is relevant for the demand controlled or need controlled function can be stored and derived based upon the measured values obtained from the sensor 3 or parameters derived therefrom. As a function of the development and expression of pathological features in the feedback signal in the embodiment described in section 4.3 hereof (below), the demand or need controlled timing of a stimulus signal is outputted at the electrodes 2 so that a stimulation of the brain tissue is effected.

The device of the invention, thus has means which is capable of recognizing the development and/or expression of the pathological features in the feedback signal measured by sensor 3. The control unit 4 is so programmed that for the timing of the embodiment described in section 4.3, the control unit 4 produces a stimulation signal which is outputted at the electrodes 2. The control unit 4 can be thus programmed for the periodic stimulation described in section 4.4 with a demand or need stimulation amplitude, the control unit 4 will at specific, preferably periodically sequenced time points, generate a stimulation signal with the amplitude calculated by the control unit 4 and deliver it to the electrodes 2. In a less preferred embodiment the control operates without demand control or need control, that is without feed back control and generates as described in section 4.2, stimulation signals which are delivered to the electrodes 2.

The control unit 4 can for example comprise a chip or another electronic device with comparable computing power.

The control unit 4 controls the electrodes 2 preferably in the following ways. The control data is reproduced by the control unit 4 to an optical transmitter 5 for the stimulation which, through the light conductor or waveguide 6 controls the optical receiver 7 because of the optical coupling of the control signals to the optical receiver 7, a galvanic decoupling of the stimulation control of the electrodes 2 is effected. This means that the effect of noise signals from the signal processing unit and control 4 into the electrodes 2 can be prevented. As the optical receiver 7, for example, a photocell can be considered. The optical receiver 7 transmits the stimulation signals received via the optical transmitter 5 for stimulation, to a stimulator unit 8. Via the stimulator unit 8, the targeted stimuli are applied through the electrodes 2 to the target region of the brain. For the case in which measurements are also to be made be the electrodes 2, apart from the optical stimulation transmitter 5, a relay 9 is also connected to the optical sensor which prevents the incursion of noise signals. The relay 9 or an equivalent transistor ensures that the neuron of activity can be measured again directly after each stimulus without overriding the isolating amplifier. The galvanic decoupling does not necessarily require an optical coupling of the control signals. Rather other alternative control systems can be provided. These can for example involve acoustic coupling, for example in an ultrasonic range. A noise free control can also for example be realized with the aid of appropriate analog or digital filters.

Furthermore, the device according to the invention is preferably provided with means for visualizing (displaying) and processing the signals as well as for data security 13 utilizing a telemetry Receiver 12. The unit 13 can be provided for the data analysis in the method described below.

In addition, the device according to the invention, using the telemetry receiver 13 can be connected to an additional reference data base to assist for example in the monitoring of the device and for carrying out the control mechanisms described in sections 5.1.2 hereof for efficient modification of the parameters. For example, as described in section 5.1.2.2.2 (below), the minimum number of individual pulses of the high frequency pulse train can be raised or lowered in order to increase or reduce the strength of the desynchronizing effect of the stimulation.

Figure 2A:
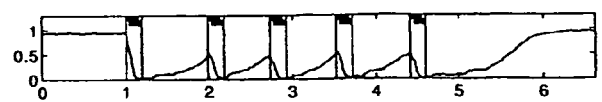
FIG. 2a illustrates the time course of the amplitude of the local field potential measured by the sensor 3 during the demand-controlled timing.
Figure 2B:
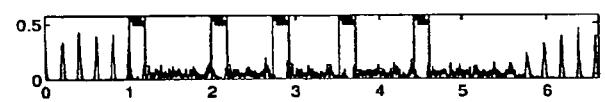
FIG. 2b illustrates the time course of the discharge pattern measured via sensor 3 of the nerve cells during the demand controlled timing.
Figure 4A:
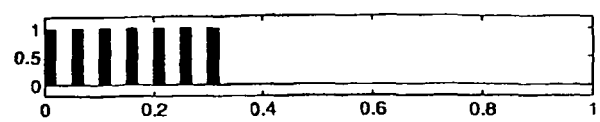
FIG. 4a through 4d illustrate an example of an excitation application with four electrodes.
Figure 4B:
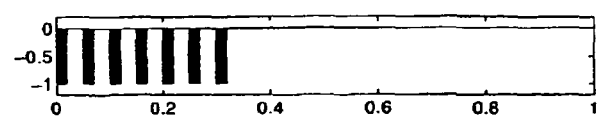
Figure 4C:
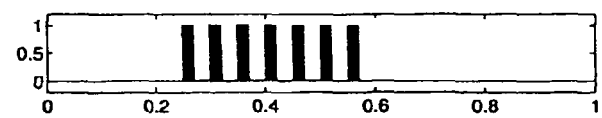
Figure 4D:
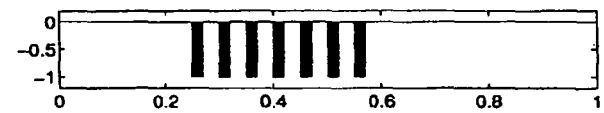

In FIGS. 2a and 2b, the abscissas give the time axis in seconds while the ordinates display the amplitude of the local field potential (FIG. 2e) or the neuronal discharge pattern (FIG. 2b) each in optional units. The amplitude of the local field potential (FIG. 2a) measured by sensor 3, service as the feed back signal for the need controlled or demand controlled timing. Whenever a threshold of the feedback signal is reached the next stimulation with the same excitation pulse is effected. The vertical lines symbolize the beginning and end of the applied excitation pulses of four electrodes 2. The latter have been shown in FIGS. 4a through 4d and comprise two time-offset pairs of high frequency pulse trains each pair is comprised of two high frequency pulse trains of different polarities. The bars between the vertical lines in FIGS. 2a and 2b symbolize the both airs of high frequency pulse trains:

The upper bar corresponds to the pair illustrated in FIGS. 4a and 4b, the lower bar belongs to the pair in FIGS. 4c and 4d.

Figure 3A:
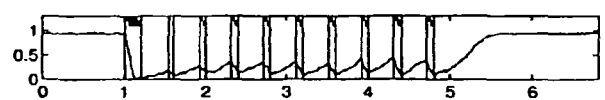
FIG. 3a illustrates the time course of the amplitude of the local field potential measured by sensor 3 during recurrent application with demand control excitation or stimulation amplitude.
Figure 3B:
FIG. 3b illustrates the time course of the discharge patterns of the nerve cells measured by sensor 3 during recurrent application with demand control stimulation amplitude.

FIGS. 3a and 3b indicate the time axis along the abscissa in seconds while along the ordinates the amplitude of the local field potential (FIG. 3a) and the neuronal discharge pattern (FIG. 3b) are given in optional units.

The amplitude of the measured local field potential from sensor 3 (FIG. 3a) serves as the feedback signal for the periodic application of the stimulus with demand- or need control stimulation amplitude. The high frequency pulse trains shown in FIGS. 4a to 4d are periodically applied, whereby within one of the total stimuli applied via the four electrodes 2 the lengths of all four high frequency pulse trains is identical and matches the measured local field potential prior to the stimulus application. The vertical lines symbolize the beginning and end of the stimulus applied by the four electrodes 2. The latter have been shown in FIGS. 4a through 4d and are comprised of two time-offset pairs of high frequency pulse trains. Each pair is comprised of two high frequency pulse trains of different particularity. The bars between the vertical lines in FIGS. 3a and 3b symbolize the two pairs of high frequency pulse trains: The upper bar corresponds to the pair shown in FIGS. 4a, 4b, the lower bar belongs to the pair shown in FIGS. 4c and 4d. The demand controlled selected lengths of the high frequency pulse trains are symbolized by the lengths of the upper and lower bars in FIGS. 3a, 3b.

In FIGS. 4a through 4d the abscissas of the time axes are given in seconds while the ordinates are shown in optional units to indicate the strengths of the individual pulses for example in the sense of the applied currents. For better visualization, the individual pulses have been filled in in black. Over the first two electrodes 2 the same high frequency pulse trains but with different polarities are applied (FIGS. 4a, 4b). The same pair of high frequency pulse trains but with a time delay are applied to a third and fourth applied electrodes.

In FIGS. 5a through 5d the abscissas are the time axes in seconds while the ordinates show the strength of the individual pulse, for example, in the sense of the applied current in arbitrary units. For better visualization the individual pulses have been filled in in black.

Figure 5A:
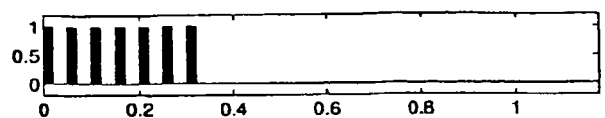
FIG. 5a through 5d illustrate an example of a time offset application of identical high frequency pulse trains to four electrodes.
Figure 5B:
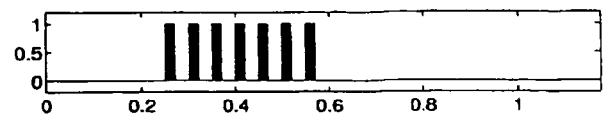
Figure 5C:
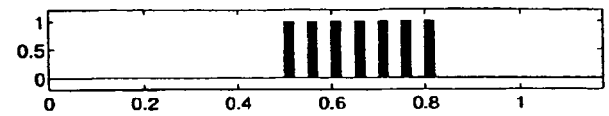
Figure 5D:
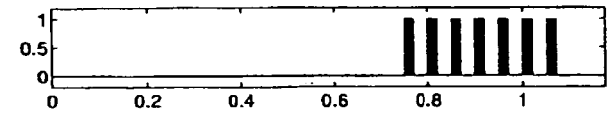

By means of the first two electrodes to the same high frequency pulse train with the same polarities are applied (FIGS. 5a, 5b) the same pair of high frequency pulse trains in a time delayed manner are applied by means of the third and fourth electrodes (FIGS. 5c and 5d).

Below the device of the invention and its functioning will be described in greater detail by way of example.

The device of the invention and its control are equipped with means to enable all steps of the method of the invention to be carried out. With the disclosed method steps, therefore, the means for carrying them out with the device is implicitly disclosed as well. The method steps present simultaneously are functionalized description of the features of the device.

According to the invention, the electrodes are introduced into the brain region which is answerable for the formation of the pathological pattern. At least two, preferably four, or even three or more electrodes are introduced according to the invention either directly in the region or in one or more regions connected with the region having the nerve cell populations or nerve fiber bundles which are responsible for the pathological pattern. The number of electrodes is only limited in that no optionally high density of electrodes can be provided in any single brain region without unnecessarily damaging the tissue and introducing a risk of bleeding in the implantation of the electrodes. In any case, the number of electrodes in the region can be N where N is greater than or equal to 2. Each electrode thus outputs in its vicinity a signal which is effective either directly in its surroundings or is conducted by a nerve fiber bundle into another area in which it can bring about a resetting of the neurological activity. The electrode signals which can give rise to a reset are already known to the skilled worker in the art:

It can for example be an individual pulse or high frequency pulse train with a pulse rate greater than 100 Hz. The device of the invention enables, via its control the selection of which of the at least two electrodes 2 will effect the reset either in its immediate environment and/or by conduction of the stimulation through a fiber bundle to another brain area.

According to the invention, N electrodes, where N is greater than or equal to 2, are so controlled that a phase shift in time of the individual electrode signals by T/N is provided to the extent that the stimulating electrodes 2 are to be found in the area to be desynchronized. T is, as is described below, the period of the rhythmic activity to be desynchronized. In case at least one of the stimulating electrodes 2 are not located in the area to be desynchronized, in the control of such an electrode 2 the transit time between the location of the stimulation and the location of the neuron population to be effected by the stimulus is taken into consideration. This is described in section 5.2 below. The device of the invention has a control which in the case of N electrodes is able to stimulate them for substantially each a Nth of the period of the activity to be desynchronized with the time shifted reset signal. The phase shifting in time can be advantageously substantially equidistant. By the phase shifting we understand the difference between the phases of the rhythmic activity to be desynchronized as influenced by the different electrodes 2. Surprisingly, with this equidistant phase shifted electrodes 2 acting upon the neuron populations respectively affected by them, a desynchronization of the entire neuron population to be desynchronized can be effected together with a suppression of the pathological symptoms. If at least one electrode 2 is outside the area to be desynchronized, the effect of indirect stimulation must be considered as has been described in section 3.2 hereof. This is developed in greater detail in sections 3.3, 3.4 and 5 hereof.

With the new method and the new device, the desynchronization is carried out qualitatively differently from that of the above described state of the art. Instead of applying signals synchronously to a pathologically effected nerve cell group in a vulnerable phase of its rhythm, the nerve cell group is simply with time coordination stimulated at a number of locations in a manner which causes the desynchronization to arise. For this purpose at the individual stimulation locations either electrical, individual or single pulses can be used or a low frequency stimulation sequence or a high frequency stimulation sequence can be used. It is essential that at least two and preferably more than two stimulation locations be stimulated. If N stimulation locations are stimulated the entire nerve cell population to be desynchronized is subdivided into substantially N equidistant subpopulations (in the phase cycle). That mean that the phases of the neuronal activity of the subpopulations follow one another in substantially equidistant steps of $2\pi/N$, $2\pi$ is the length of a period which has also bee defined above as the phase cycle. This utilizes the fact that the pathologically increased interaction between the neurons can contribute to the desynchronization. In this case one utilizes the surprising presence of a self organization process of the neuronal population which is answerable for the pathological synchronization to assist in eliminating it. The same applies where the subdivision of the subpopulations is on an equidistant basis, that is that the subdivision of the total population into subpopulations is effected so that the phases therein will be equidistant and a desynchronization will be accomplished. In contrast thereto, without a pathologically increased interaction, no desynchronization will be effected. The energy of the system itself is thereby utilized to produce a therapeutic effect an equidistant division into subpopulations is much more easily brought bout in a complete desynchronization as with the described methods as the state of the art. The best results are obtained when an equidistant phase shift or a substantially equidistant phase shift of the phase resetting stimuli is applied. From a treatment point of view it is of greater advantage still when the stimulating pulses outputted by the electrodes have the phases of the stimulated subpopulations at least partially shifted relative to one other. The treatment results are better as the phase shift produced approaches an equidistant phase shifting.

1. Mechanism of the Stimulation:

The goal of the stimulation is to counteract a pathologically created synchronization in a nerve cell population by desynchronization. For this purpose, the nerve cell population to be desynchronized is so influenced at at least two locations by the phase shifted stimulation at different places in the brain that primary at least two subpopulations of the total nerve cell population are formed. Because of the pathologically created interaction between the nerve cells the state created by the stimulation is unstable in at least these two subpopulations and the entire nerve cell population have quickly approaches a state of complete desynchronization. The desired state, that is the complete desynchronization is thus not present immediately after the application of a stimulation but typically develops over a short period, usually not less than one period of the pathological response. With the desynchronization methods described in the prior art, the nerve cell population to be desynchronized is directly brought into a desynchronized state. This however only occurs by an adequate selection of the stimulation parameters whereby these must be precisely calibrated and can only have limited tolerances.

The device according to the invention by contrast stimulates the nerve cell population to be desynchronized in a qualitatively different manner: by the coordinated timed stimulation of subpopulations, the nerve cell population to be desynchronized is split into at least two subpopulations. This process functions for a greater range of the stimulation parameters and requires no expensive calibration and can involve much larger tolerances. The reasons for this is that unlike the state of the art described previously, the invention does not require the presence of a vulnerable phase which can make up only about 5% of a period of the rhythm to be desynchronized. Rather the stimulation operates independently from the dynamic starting state.

2. Type of the Individual Stimulation:

As an individual stimulus or single pulse, a stimulus is intended which can be applied by a single electrode 2 in contrast with a single stimulus reference may be made herein below to a single pulse whereas the single stimulus may be an individual pulse shaped monophasic or biphasic stimulus.

A single pulse can either be a single stimulus or part of a high frequency or low frequency pulse train. For a stimulation which is coordinated in time over at least two electrodes, individual stimuluses are used which are recognized by the skilled worker in the art as for example:

a) electrical monophasic or biphasic single pulses;

b) electrical high frequency pulse trains with a pulse rate of preferably more than 100 Hz, whereby the single stimulus of the pulse train can be monophasic or biphasic individual pulses;

c) electrical low frequency pulse trains whereby with a pulse rate f in the order of magnitude of the frequency g of the rhythm to be desynchronized, monophasic or biphasic individual pulses or a brief high frequency pulse train can be applied of less than preferably one to twenty monophasic or biphasic individual pulses. In this case the frequency of the pulse rate of the low frequency train is given advantageously substantially by the ratio $f/g=n/m$, whereby n and m are small whole numbers preferably 1, 2 or 3;

d) apart from the substantially periodic sequences of individual pulses in a high frequency pulse train or low frequency pulse train given in b) and c) above, the point in time of the application of the individual pulses in a pulse train can also vary stochastically [randomly] and/or deterministically.

Under "coordinated stimulation with time" a condition will be understood in which the individual stimuli are applied to the respective electrodes 2 at respective points in time, which possibly are different from one another, as described in Section 4.1 (below) in order to produce between the stimulated subpopulations the phase difference with the therapeutic effect for the neuron population to be desynchronized. The device is thus provided with means which can apply the described electrical monophasic and/or biphasic individual pulses and/or electrical high frequency pulse train and/or electrical low frequency pulse train of the described types. The means are the electrodes 2 and the control 4 which outputs control signals to the electrodes 2 for triggering these stimuli.

As the total stimulus, the individual stimuli applied via the electrodes 2 are intended which, according to the mechanism by which the device of the invention operates, evokes a desynchronization in the neuron population to be desynchronized. Examples of total stimulus are shown in FIGS. 4a through 4d and FIGS. 5a through 5d. In the framework of a total stimulus, preferably a single stimulus is delivered by each electrode.

With repetitive applications of the total stimulus, the electrodes 2 which are effective in the framework of the total stimulus can be varied. Especially a part of the electrodes 2 which receives the respective total stimulus can be controlled or varied based upon the selection made with a stochastic [random] and/or deterministic algorithm.

3. Number and Spatial Arrangement of the Electrodes 3.1 Number of Electrodes:

The number of electrodes used is a compromise of 2 contrary requirements or desiderata:

On the one hand the neuron population to be desynchronized by the stimulus should be divided into the greatest number of functional subpopulations as possible. This can be achieved by providing as means electrodes as possible for the stimulation. On the other hand, the number of electrodes to be implanted should be held as small as possible in order to avoid unnecessary tissue damage and above all to avoid bleeding in the brain during the implantation. For example, at least two electrodes are used. Three electrodes can also be used. Especially preferred is the use of four electrodes since the desynchronization with four electrodes is more pronounced and lasts longer. With the increase in the number of electrodes to, for example, at least two electrodes are used. Three electrodes can also be used. Especially preferred is the use of four electrodes since the desynchronization with four electrodes is more pronounced and lasts longer. With the increase in the number of electrodes to, for example, 5, 6, 7, 8, 9 up to 100 or more, the desynchronization effect becomes more pronounced and the duration is improved. The use of a large number of electrodes, for example, 100 electrodes can only be realized with microelectrodes and modern neurochip technology.

3.2 Definition of the Concept:

In the following, by the term "target population" the nerve cell population which will be stimulated directed by an implanted electrode will be understood.

A target population is thus directly stimulated by an electrode implanted at all or nearby.

The nerve cell population which is pathologically synchronously active is indicated as the area to be desynchronized or as the nerve cell population to be desynchronized. The latter is not anatomically bounded; rather it can include at least one component from the following group:

at least a part of at least one anatomic area, or at least one complete atomic area.

The area to be desynchronized can be either directly or indirectly stimulated.

Direct stimulation by a stimulation electrode 2:

In this case, the stimulation electrode 2 is located in the area to be desynchronized. This electrode 2 effects thereby the target population which is found in the area to be desynchronized.

Indirect stimulation by a stimulation electrode 2: In this case the area to be desynchronized is not directly stimulated by means of electrode 2. Rather a target population or a fiber bundle, stimulated by the stimulation electrode 2 is functionally tightly connected with the area to be desynchronized and delivers the desynchronizing stimulus thereto. In this case, the stimulation effect is communicated to the area to be desynchronized preferably by an anatomical connection. For the indirect stimulation, the term target area will thus refer to the target area population and the communicating fiber bundle. The term target area in the following will be understood to mean the area to be desynchronized and the neuron populations functionally tightly connected thereto and any connecting fiber bundle.

The stimulation mechanism according to the invention is intended to stimulate the neuron population to be desynchronized by the individual electrodes at given, typically different points in time within a period of the oscillating activity of that neuron population. The time spacing between individual stimuli are fractions of the period of the oscillating activity to be desynchronized and amount preferably to substantially a Nth of the period where N is a small whole number, for example, 4. N is thus a whole number which is preferably below 1000, even more preferably less than 100 and especially can be less than 10. The period of the oscillating activity to be desynchronized which serves as the time reference for the application of the individual stimuli is designated as the stimulation period T. The term stimulation T is thus central for the functioning of the invention as is set out in section 5.1.2.2.2 (below) describing the process following the stimulated period T which is neither adjusted by calibration nor by measurement during the stimulation operation but rather is imposed by the neuron population to be desynchronized.

Under the term "rhythm" will be understood the rhythmic and thus approximately periodic neuronal activity which amounts to a pathological superimposition of synchronous activity on the nerve cells. A rhythm can last a long time or appear only briefly. A reset of a neuron population will be understood to mean the reset or restoration of the phase relationships of the natural activity of this neuron population.

3.3 Embodiment for the Case in which all Electrodes are Positioned in the Nerve Cell Population to be Desynchronized:

The N electrodes should preferably be so arranged that with each individual electrode a Nth of the nerve cell population to be desynchronized is directly stimulated. This can be realized with different numbers of electrodes and different geometrical arrangements of the electrodes with respect to one another. For example, an optional unsymmetrical arrangement can be selected. Preferred, however, is a substantially symmetrical arrangement since in this case the stimulation, directed functional division into subpopulations enables the smallest current input to be experienced. For example, the end points of the electrodes projected among the electrodes can give a square. For example, six electrodes can also be used. In that case, four are preferably arranged in a square pattern in one plane while the other two substantially equidistantly perpendicular to this plane whereby its connection lie forms substantially a rotation axis for the four electrodes arranged in a square. For the greatest effect in various geometric arrangements the electrodes at least partly can have different lengths.

3.4 Embodiment for the Case that at Least One of the Electrodes is not Positioned in the Nerve Cell Population to be Desynchronized.

In this stimulation configuration, at least one target area different from the area to be desynchronized is stimulated. As has been described in section 3.2 above, the indirect stimulation is communicated to the nerve cell population to be desynchronized from the various neuron populations and/or the stimulation of the nerve cell population to be desynchronization is carried out by the fiber bundles connected therewith.

Thus in a target area or in the area to be desynchronized either at least one electrode or a multielectrode arrangement in the sense described in section 3.3 above can be used.

4. Demand Controlled or Need Controlled Application:

4.1 Pattern and Polarity of the Stimulus:

In the framework of the application of a stimulus, through each individual electrode 2 an individual stimulus is applied. The individual stimuli can have the forms described in section 2 hereof above.

The individual stimuli applied via the various electrodes 2 can however although they need not, differ in type and/or energy input. For this purpose, the device according to the invention is capable, with respect to its control, to be so programmed that it can vary the type and/or the energy input of the individual stimuli.

The individual stimuli applied through an individual elected in the repeated application of the stimulus need not however have its type and/or energy input varied. For example, in the case of a direct stimulation with N electrodes, each can have the same individual stimulus applied with a time delay of respective T/N whereby T is the stimulation. For example, N=4 the time spacing of the individual stimuli will follow at T/4 after one another over the first, second, third, fourth electrode 2 as illustrated in FIGS. 5a to 5d. For this purpose, the device of the invention has a control which is so programmable that the N electrodes 2 are triggered with a time delay of substantially T/N for individual stimulus application.

Alternatively, thereto, for example with the demand control timing described in section 4.1 above, especially, the sequence of the individual stimuli can be controlled systematically within the total stimulation or randomly that is in accordance with a deterministic or stochastic law. For this purpose, the device according to the invention is equipped via its control which can be so programmed, that it controls the sequence of the individual stimuli can be controlled systematically within the total stimulation or randomly that is in accordance with a deterministic or stochastic law. For this purpose, the device according to the invention is equipped via its control which can be so programmed, that it controls the sequence of the individual stimuli within a total stimulus deterministically and/or stochastically.

By varying the sequence of the individual stimuli within the total stimulus, adaptation processes in the neuron population which have required increases in the stimulation intensity to reach the same therapeutic effect over time, are bypassed.

As a further additional possibility, time delays in the stimulus application can be replaced by alternations of the polarity of the individual stimuli. For this purpose, the device of the invention is equipped, through its control which can be so programmed, that it can control at least one of the electrodes 2 so that alternating polarities are applied thereto. For example, is N=4 over the first and second electrodes two and after a time delay of T/4, over the third and fourth electrodes 2 respectively a pair of monophasic or biphasic individual pulses of opposite polarities can be applied as has been illustrated in FIGS. 4a to 4d for the monophasic individual pulses.

4.2 Non-Demand Controlled Stimulus Application.

The total stimulation described under section 4.1 hereof can be applied in a simpler embodiment without demand control. In this case, the total stimulation can be strictly periodic in time or nonperiodic in time. In this embodiment, the device according to the invention is equipped, over its control, and so programmed that it does not enable demand controlled application of the total stimulus. The total is then so programmed that it is capable of outputting the total stimulus periodically and/or nonperiodically. A nonperiodic sequence in time of the total stimulus can be generated in a stochastic process.

4.3 Demand Controlled Timing:

Under the "timing", the timing pattern of the stimulus application is meant.

With sensor 3, the feedback signal resulting from the activity of the neuron population to be desynchronized is measured. This feedback signal is fed back to the unit 4 for processing and regulation 9 the means for recognizing a pathological feature of characteristic. As soon as the unit 4 for signal processing and/or regulation recognizes the pathological signal, a stimulus is applied. By a pathological feature, should be understood, for example, one or more of the following characteristics of the feed back signal:

(a) The amplitude of the feedback signal exceeding a threshold value. The device of the invention is thus in a preferred embodiment equipped with means for recognizing as threshold value of the feedback signal. In this case, preferably the feedback signal itself or its magnitude or an amplitude can be compared with the threshold value. The means for recognizing the threshold value can in this embodiment be so programmed that it compares the feedback signal there is and/or a value of at and/or an amplitude thereof with the threshold value. To determine the amplitude, in a simple version one can determine the value of the signal or utilizing band pass filtration and a subsequent Hilbert transformation for wavelet analysis. The unit 4 for signal processing and/or regulation is so programmed in this case that it can determine the magnitude of the signal and/or the result of a bandpass filtering and carry out a Hilbert transformation or a wavelet analysis.

The feedback signal or its magnitude are used especially preferably since the calculation of the amplitude requires a significantly higher expenditure of computing resources and the precision of this calculation depends upon the correct choice of the algorithm parameter.

In addition, the determination of the amplitude cannot be carried out on a single measurement value of the feedback signal but must be carried out at sufficiently large time intervals within the skill of the worker in the art.

Through this type of analysis of the feedback signal in a sliding window, the recognition of the pathological feature is somewhat delayed. The form of analysis described in part (a) hereof of the shape of the feedback signal is to be used when the pathological activity to be desynchronized is exclusively measured by the sensor 3 or predominantly measured by the sensor 3.

(b) In case the sensor 3, in addition to this activity additionally measures non illness specific activity; regulating unit 4 produces a recurrent, preferably periodic stimulation whose strength of the stimulus applied at each respective point in time dependent upon the expression of the pathological feature in the feedback signal. For this purpose, the intensity or the duration or—when pulse trains are used—the number of individual pulses of the pulse train is matched to the expression of the pathological feature. In a time window of freely selectable and preferably constant length, which ends at a constant time spacing before the respective stimulus, the expression or the pathological feature is determined in the following way:

(a) In the case in which a sensor 3 exclusively or predominantly measures the pathological activity to be desynchronized the amplitude of the expression of the synchronization in the neuron population to be desynchronized corresponds to the measurement. The amplitude thus represents the pathological feature. The amplitude can be estimated from a determination of the maximum of the signal or using the mean value of the magnitude of the signal or with band pass filtration with subsequent Hilbert transmission or wavelength analysis.

The first two variants (determining the maximum of the signal or determining the mean value of the signal) are used especially preferably since the calculation of the amplitude by means of a Hilbert transformation wavelet analysis requires a significantly higher expenditure of computer resources and the precision dependent upon the correct choice of the algorithm parameters.

(b) In case the sensor 3 measures, apart from the illness specific activity additionally also nonillness specific activity, from another neuron population, for the estimation of the expression of the pathological feature the feedback signal cannot directly be used. Since the illness specific activity typically arises in a frequency range different from the frequency range of the known illness specific activity the estimation of the activity of the illness specific range is carried out in this case. This can be achieved for example by a frequency analysis. For example the spectral illness in the illness specific range can be determined. Alternatively after band pass filtration the amplitude can be determined by measuring the maximum of the band pass filtered signal or the average value of the magnitude of the signal or after a subsequent Hilbert transformation or by wavelet analysis.

4.5 Establishing the Demand or Need:

On at least two grounds, there is no stronger relationship between the expression of the pathological feature and the expression of the illness specific symptom. Firstly, there is a spacing of the sensor 3 from the area in which the feedback signal should be generated and which effects the amplitude in the illness frequency range. Secondly, for a certain expression of the illness specific feature, that is the expression of the rhythmic activity in the illness specific frequency range, is not singular with the illness specific symptom. Since the illness specific rhythm acts on and through over complex nerves complex in the brain the dynamic relationship is not a linear one and thus there is no fixed relationship between the pathological rhythm and the expression of the symptom. When for example the pathological rhythm does not sufficiently coincide with the biomechanically given intrinsic frequency of an extremity, the tremor produced by the pathological rhythm is sufficiently the case when the pathological rhythm is in resonance with the biomechanically determined intrinsic frequency of the extremity.

The measurement for a given location of the sensor 3 provides a feedback signal which will be understood by the skilled worker to like within an experience range. The value of the expression and the feedback signal measured by the sensor 3 as to the pathological feature, when it exceeds the threshold typically representing the development of symptoms for tremors is used. The threshold is a parameter which is utilized in the embodiment described in section 4.3 as the basis for the need controlled time. The device of the invention thus includes means for detecting or provide a threshold value. With the need control timing the advance is gained that the effectiveness does not depend critically upon the selection. Rather the threshold changes can be made with large tolerances which can be upped to 50% of the maximum expression of the illness specific feature.

The choice of the threshold can either be intraoperative or made in the first days after the operation by measurement of the signal over the sensor 3 and determination of and monitoring of the expression of the illness specific feature and its comparison with the expression of the symptom for example the degree of shaking or tremor.

In a further preferred embodiment, as the threshold representative value is selected, for example, the mean value of thresholds of patients over a collection of patients.

In the embodiment described in section 4.4 the recurrent stimulation with need controlled stimulation strength, no threshold is necessary.

5. Calibration and Regulation.

5.1 All Electrodes 2 Lie in the Neuron Population to be Desynchronized.

5.1.1 Stimulation Parameter for the Beginning of Stimulation:

5.1.1.1 frequency selection of the frequency without prior operation of the device: The frequency range of the pathologically neuronal activity is known for respective pathological images by the skilled worker in the art (Elble R. J. and Koller E. C. (1990): Tremor John Hopkins University Press, Baltimore). From this frequency range, preferably the average value can be taken. Alternatively, instead of this average value, from a database, the frequency can be chosen which is the expected value based upon the age and the specific disorder and its severity.

It is not necessary for the effective operation of the device according to the invention that the frequency given at the outset coincide with the actual frequency of the neuron population to be desynchronized. The regulation which is described hereinafter under 5.1.2.1 of the stimulation period T functions also when the correct frequency value deviates greatly from the starting value. The reference to a strong deviation includes a value which may be by a factor of at least 10 fold too large or too small. Alternatively one can begin with a frequency value known to the worker in the art which is a typical frequency range for the illness.

Selection of the frequency with prior operation of the device: As the starting value for the frequency the mean value or average of the frequency during the previous operation of the device is selected in both cases that with and without previous operation of the device the stimulation period T is calculated as the inverse of the starting value of the frequency.

5.1.1.2 Intensity:

5.1.1.2.1 Demand-Controlled Timing:

The starting value of the stimulation parameter which determines the intensity of the individual stimulation for example length of the high frequency pulse train, an amplitude and duration of the individual pulse and pause for interval between individual pulses. Of the individual pulse of 60 to 200 is, a rate of the individual pulses of 120 Hz, an amplitude of 4 volts. The starting values for the frequency and intensity can be thus previously given and need not be determined, especially using time consuming calibration.

5.1.1.2.2 Recurrent Application with Need Controlled Stimulus Strength.

The starting values of the stimulation parameter which determines the intensity of the maximum stimulus (length of the high frequency pulse train, amplitude and duration of the individual pulses and interval between individual pulses) are selected by the artisan based upon known experiential ranges (for example, a high frequency pulse train with two individual pulses, individual pulse duration of 60 to 200 Ps, rate of individual pulses 120 Hz amplitude 4 volts).

The starting value of stimulation parameter which determines the intensity of the minimum stimulus (for example length of high frequency pulse train amplitude and duration of the individual pulses and interval between pulses) is determined by the artisan experientially, (for example a high frequency pulse train with three individual pulses, individual pulse duration of 0 to 200 ps, rate of the individual pulses 120 Hz V volts).

5.1.2 Regulating Mechanism of the Device According to the Invention or its Control During the Stimulation.

5.1.2.1 Matching the stimulation period T:
in the target area or an area closure connected therewith, the feedback signal is measured. For example in Parkinson instead of a measurement by the stimulation electrodes, a measurement can be carried out of the activity in the adjacent area, for example, the promoter cortex, using epicordical electrodes. In a time window with the length given below, the dominant mean frequency is determined. For this purpose different algorithms can be used. For example the frequency can be determined as the inverse of the instantaneous period whereby the instantaneous period is obtained from the time difference between maximum of the feedback signal which follow one another. In case the sensor 3 does not measure only illness specific activity, for this type of frequency estimation the illness specific activity must be first extracted by a band pass filter for the illness specific frequency range. Alternatively, for example the frequency can be estimated by the technique described in section 4.3 hereof. The stimulation period T is taken as the inverse of the mean frequency.

The time window for this frequency estimation which can be open toward the upper values, can be for example ten thousand periods, preferably one thousand periods, and especially preferably one hundred periods of the illness activity or also some other optional value.

5.1.2.2 Demand or Need Control

5.1.2.2.1 Demand or need controlled timer.
When the feedback signal exceeds stimulation is effected this purpose the device detecting a crossing of signal to the electrode that is that the target and the feedback signal the threshold values the respective next preferably with the same stimulus. For is provided with a control which after the threshold value outputs a stimulating 2. If the desired effect is not obtained, population is not sufficiently disclosed does not fall back below the threshold value, the strength of the stimulus is raised to a maximum value that is selected based on safety, for example in steps of 0.5 volt per 50 periods.

For this purpose the device of the invention is provided with a control which can recognize the change in the feedback signal and in the absence of a change in the feedback signal will match the stimulating signal values as described previously. After for example 20 stimuli, the device can begin to slowly vary the setpoint value (for example in steps of 0.5 volt per 200 periods) to raise it as long as the simulation is effective. The stimulation effect can be determined as in section 4.5 hereof. The control is thus so programmed that it recognizes the change in the feedback signal and thus the stimulation effect.

5.1.2.2.2 Repeated Application with Demand Controlled or Need Controlled Stimulation Strength:

5.1.2.2.2.1 Rapid Control:
The time interval between the individual stimuli are substantially whole number multiples of the stimulation period T. That means that the time interval between the beginning or preferably the end of the application between stimuli following one another is given by $$t_{j+1} - t_j = N_j T \quad \text{Formula 1}$$

In Formula 1, $t_j$ is the time point of the beginning or preferably the end of the 11111 stimulus. T is the stimulation period and $N_j$ is a whole number. The time period given by $t_{j+1} - t_j$ must not, as defined in Formula 1, strictly correspond to a whole number multiple of T but can also be given in accordance with $$t_{j+1} - t_j = N_j T + x_j \quad \text{Formula 2}$$

whereby $x_j$ is small by comparison to the stimulation period T. The device according to the invention comprises, in one embodiment, a control which preferably outputs the stimuli to the electrodes 2 in time frames or time compartments which are substantially whole number multiples or integral multiples of the stimulation period T. Basically all imaginable variations of time intervals are possible but a substantially strictly periodic application of the stimuli is preferred. That means it is preferable to provide a constant number sequence like for example $N_1$, $N_2$, $N_3$, where $N_j = N$ for all $j=1, 2, 3$ etc. With a number sequence like $N_1$, $N_2$, $N_3$, etc, a constant number sequence can be deviated from for example by the use of a periodic, quasiperiodic, chaotic or stochastic [random] programming.

The strength of the individual stimulus is matched by the control of the invention to the expression of the pathological feature in the feed back signal for example in the following way:

In a time window before the application of the stimulus, the expression of the pathological feature of the feed back signal is estimated as in Section 4.4 hereof above. For that purpose, for example, the amplitude of the oscillating activity in the pathology specific frequency range is determined by an averaging of the magnitude of the corresponding band path filter feed back signal in a time window prior to the stimulus application. The strength of the stimulus used is determined by the expression of the pathological feature as described in Section 4.4. As the pathological feature is expressed more strongly so the applied stimulus will be stronger. The control according to the invention is thus so programmed in this embodiment that it increases the energy input and the strength of the stimulus signal at the electrode 2 with the increasing magnitude of the feed back signal. The relationship between the expression of the pathological feature and the stimulus strength can in the simplest case be linear, although it can also have a complex form, for example a nonlinear form. The stimulus strength can be varied by varying different stimulation parameters like the number of individual pulses in high frequency pulse train or low frequency pulse train or the amplitude of the individual pulses for the duration of the individual pulses. Preferably the number of individual pulses in the high frequency pulse train will be varied.

The number of individual pulses in the high frequency pulse train which are applied to the $k^{th}$ electrode 2 in the frame work of the $j^{th}$ total stimulation is indicated as $M_j^{(k)}$ can be carried out separately for the individual electrodes 2. Preferably however the matching is carried out for all of the electrodes 2 in the same manner. That means that $M_j^{(k)} = M_j^{(l)}$ for $k, l = 1, 2, 3, \ldots, N$ whereby N is the number of electrodes 2. In this case the number of the individual pulses of the high frequency pulse train is given by $M_j = M_j^{(k)}$ for $k = 1, 2, \ldots, N$. The device of the invention is thus so programmed that it can vary the stimulation strength in the indicated manner.

As has been described in Section 4.4 above, the expression of the pathological feature, for example, as the amplitude of the oscillating activity in the pathologically specific frequency band, is determined. For this purpose, for example in a time window before the application of the $j^{th}$ stimulus, the magnitude of the illness specific frequency range band path filter signal is determined. The value determined in this matter is indicated as $A_j$.

The relationship between the number of individual pulses in the high frequency pulse train $M_j$ and the amplitude $A_j$ can be given, by way of example, by $$M_j = A_j \frac{M^{max}}{A^{max}} + M^{min} \qquad \text{Formula 3}$$

whereby $M^{min}$ is the minimum number of the individual pulses in the high frequency pulse train.

The quotient $M^{max}/A^{max}$ is apart from $M^{min}$ the second parameter which is set. $M^{max}$ and $A^{max}$ are values which are within the experience of the skilled worker in the art and allow the definition of the quotient $M^{max}/A^{max}=C$. Formula 3 determines the rapid control for each stimulus, providing the requisite stimulus strength, in this case through the number of individual pulses of the high frequency pulse train Mj matched to the actual value of the amplitude $A_j$.

5.1.2.2.2.2. Slow Regulation Control:

The above given parameters $M^{min}$ and C can be set either manually or adjusted for the device according to the invention in the course of slow regulation.

The slow regulation can occur over a time scale which preferably corresponds to a period between 10 and 100 periods of the feed back signal. C and $M^{min}$ can be varied upwardly and downwardly in combination as well as separately. The goal of this regulation is to suppress the expression of the pathological feature in the time window of the slow regulation. By a sufficient suppression of the pathological feature, is to be understood a suppression of the feature below the threshold described in Section 4.5 hereof. Preferably exclusively the parameter fen is regulated. 5.2. At least one electrode does not lie in the neuron population to be desynchronized:

As described in Section 3.3 hereof, at least one electrode 2 may not be located in the neuron population to be desynchronized. In the case of an electron 2 which does not lie in the neuron population to be desynchronized, the neuron population to be desynchronized is influenced by indirect stimulation as described in Section 3.3 above. Since in the case of an indirect stimulation, the conduction time between the stimulated neuron for example, from other neuron populations, in the analysis of the feedback signal a further algorithmic step must be introduced.

Since the illness-specific activity typically arises in a frequency range which is different from the frequency range of the nonillness specific activity it suffices advantageously to estimate the activity in the illness specific frequency range. The frequency of the illness specific activity is for example determined from the time difference from the trigger points which arise in succession. Trigger points are characteristic points, like maxima, minima, inflection points and zero passages. Preferably this analysis is carried out in a sliding time window whereby the mean value of a multiplicity of time differences are formed, thereby increasing the stability of the frequency estimation. Alternatively, the frequency estimation can also be made by the known spectral estimation method and other frequency estimation techniques within the skill and knowledge of the worker in the art.

For this purpose the device of the invention in a special embodiment, comprises means for estimating the activity in the illness specific frequency range, for example, by the spectral estimation method, by wavelet analysis. This can for example be achieved with a frequency analysis by the means for carrying out the frequency analysis. For example the spectral energy in the illness specific frequency range can be determined in a sliding window. Alternatively, after band pass filtering the amplitude in the illness specific frequency range can be determined by first determining the maximum of the band pass filter, signal or the mean value of the magnitude of the band pass filter, or using subsequent Hilbert transformation or wavelet analysis. For this purpose the device according to the invention comprises for example, means for carrying out a band pass formation of the amplitude and means for determining the maximum of the band pass filter system and, for means for determining the mean value of the band pass filter signal and/or means for carrying out a Hilbert transformation and/or a wavelet analysis.

In the case of demand controlled timing, for example, always the same stimulus will be used. Preferably the stimulation period, as will be described in section 5.1.2.1 hereof above, will be matched to the instantaneous frequency of the neuron population to be desynchronized. To that population a stimulus is applied upon the existence of the pathological feature over the stimulation period and which is matched to the instantaneous frequency. The intensity of this stimulus remains preferably constant. Preferably the intensity is modified as described in section 5.1.2.2.1 hereof above, in accordance with the stimulation effect.

4.4 Recurrent Stimulation in Demand Controlled Stimulation Strength:

The feed back signal is measured by the sensor 3 and indicates the activity of the neuron population to be desynchronized. This feedback signal is fed to the unit 4 for signal processing and/or regulation. The signal processing and/or population on the one hand and the neuron population to be desynchronized on the other can have various values, before carrying out the desynchronization stimulation the respective conduction time is first measured. For this purpose the respective stimulation electrode 2 is stimulated and the stimulation response is measured via the electrodes which has been planted in the neuron population to be desynchronized (sensor 3). This electrode is stimulated indirectly by all of the stimulation electrode 2 and thus separately n times whereby n typically is a small whole number up to for example 200. From this the mean conduction time is estimated advantageously in the following manner. The duration between the beginning of the stimulus application over the $j_{th}$ electrode 2 and the first maximum of the stimulation response or the magnitude of the stimulation response, $T_j^{(k)}$, is determined for each individual stimulus application. In the magnitude $T_j^{(k)}$ the index j stands for the $j_{th}$ electrode 2 while the index k stands for the tape applied stimulus. From this, for each stimulation electrode 2 which is to effect an indirect stimulus, separately the mean duration between stimulus beginning and stimulus response is determined in accordance with Formula 4:

$$\tau_j = \frac{1}{L_j} \sum_{k=1}^{L_j} \tau_j^{(k)} \qquad \text{Formula 4}$$

In this Formula, $L_j$ represents the number of applied stimuli over the $j^{th}$ stimulation electrode 2. $L_j$ can, although not necessarily, be the same for all stimulation electrodes 2 through which indirect stimulation is to be effected. The conduction time $T_j$ determined in this manner for the desynchronizing stimulation, is taken into consideration in the following manner:

If in the direct synchronization of the neuron population to be desynchronized, a stimulation is to be applied at time t over the $j^{th}$ stimulation electrode, then in the case of the indirect stimulation the $j^{th}$ stimulation electrode 2 will receive the stimulus at the time $t-_{tj}$.

The determination of the stimulation parameter at the beginning of stimulation and the control mechanism during stimulation are fully analogous in the case where the conduction time $T_J$ is taken into consideration as described in Section 5.1.1 and 5.1.2 above.

5.3 Determination of the Threshold:

The parameters of the threshold described in Section 4.5 above must be selected for the demand controlled timing described for the embodiment in Section 4.3 above. In a preferred embodiment of the demand control, the threshold is either rendered intra operative or preferably determined in the first days after the operation by measuring the feed back signal over sensor 3, which is responsive to the expression of the illness specific feature, and comparing it with the expression of the sensor, for example, the degree of trembling. In a preferred embodiment the selection of the threshold is monitored at significant time intervals, for example, with half yearly monitoring. In a less preferred embodiment of the demand control timing, as the threshold a representative value, for example, a mean value of thresholds measured with a collection of patients is used.

5.4 Advantages

The calibration carried out in accordance with the invention is, by comparison with the described calibration in German patent application 102 11 766.7 substantially more rapid, less prone to failure and less expensive. It is clearly quicker since with direct stimulation without test stimuli the stimulation effect is immediately commenced and optomized as described in Section 5.1.2 hereof. With repeated stimulation with demand control stimulation strength and direct stimulation of the neuron populations to be desynchronized, no calibration is necessary. By contrast to this, in application DE 102 11 766.7, the method requires a series of tests stimulation in which the stimulation parameter is systematically varied. By contrast thereto, for conduction time determination even in the case of the indirect stimulation described above, the duration is typically less than two minutes. According to the invention at least a half hour of time is saved by comparison with the prior art calibration. Because of the more rapid calibration, the method of the invention can be used intra operatively and optimized during the placing of the deep electrodes 2. It is possible in this manner to use the affect of the desynchronizing stimulation on the expression of the sensor, for example, the tremor directly as a parameter for the correctness of electrode placement.

The calibration in accordance with the invention is less prone to failure by comparison with the calibration method of the German patent application 102 11 766.7 since the frequency and conduction time estimation used in accordance with the calibration of the invention are not treated as critical parameters as for example the limits and characteristics of the band path filter. By contrast, the calibration in the German patent application 102 11 766.7 depends critically on the parameters of the band path filter used.

In addition, the calibration according to the invention utilizes frequency and conduction time estimation which can be carried out with significantly simpler algorythms. As a consequence, the software and hardware realization is significantly less expensive.

Especially advantageous is the embodiment with repeated application with need control stimulation strength since with this method no threshold need be detected. In contrast thereto, the embodiment using need controlled timing and also the method of German patent application DE 102 11 766.7 requires threshold detection. Example:

If for example four locations are to be stimulated, by means of four electrodes the following exemplary stimuli are produced:

1. With each of the electrodes the same high frequency pulse train is applied whereby, as shown in FIGS. 5a-5d the pulse train are each offset in time by T/4 where .T is the mean period of the rhythm to be desynchronized.

2. Through the electrodes 1 and 2 high pulse trains of the same length but different polarity are applied as shown in FIGS. 4a-4d. Through the electrodes 3 and 4 the same high frequency pulse train are applied and for the electrodes 1 and 3 as well as 2 and 4, the same high frequency pulse train are used. The high frequency pulse train of the electrodes 3 and 4 are offset in time by T/4 (that is later) than the high frequency pulse trains of the electrodes 3 and 4.

Instead of the high frequency pulse train, also single pulses or low frequency pulse trains (with a frequency in the range of frequency of the neuron population to be desynchronized, is used). There are, by way of example, two different control mechanisms with which a demand control and thus energy saving and mild (side-effect avoiding) stimulation can be carried out:

1. Demand control (that is demand control selection of the time point) for the application of the total stimulus (FIG. 2): Whenever the synchronization of the nerve cell population exceeds a threshold value, the next total stimulation is outputted over all electrodes. This variant can be used preferentially when the rhythm to be suppressed does not fluate too greatly.

2. Repeated stimulation with demand control duration for the high frequency pulse train (FIG. 3):

A periodic stimulation is carried out with coordinated stimulus through all electrodes. The strength of the stimulus, that is preferably the duration of the high frequency pulse train, is matched to the strength of the synchronization of the neuron population. The stronger the synchronization the stronger the coordinated stimulus. With this variant, one can select a time delay between the individual stimuli at t/ or rather than T/4 where T is the period of the rhythm without stimulation and T the period forced on the rhythm by the stimulation. In other words, T is the frequency with which the individual stimuli are applied. The result is a forced oscillation of the system using the single critical stimulation parameter. Instead of an expensive calibration in this context it is dictated by the stimulation period. The demand control stimulation is utilized in any event since the neurons have a pathological tendency to fire periodically or in first (rhythmic production of groups of action potential). Because of this an entrainment easily can arise, that is it is simple in subpopulations to stabilize the periodic rhythm. Because of this form of stimulation requires about 1.5 times less current by comparison to demand control timing.

In both controlled methods (demand control timing and demand control strength), one can preferably match the single important stimulation parameter, the time delay between the individual stimuli, by measurement of the frequency of the nerve cell population in the target reach or another associated closely nerve cell population. In this case as well method 2 (demand control strength) has the advantage that its desynchronizing effects is stable against small errors in the frequency estimation or abrupt fluctuations of the frequency period.

The lack of a time consuming calibration and the stability of the effect even in the case of strong frequency fluctuations, especially the method 2 (demand controlled strength) has important consequences:

1. Already intraoperatively it is possible during the insertion of the deep electrode to apply the stimulation sequence and thereby monitor the effect. As a consequence, the most suitable target point can be determined more clearly. For the prior demand control processes, one required a calibration which lasted thirty minutes longer per electrode. This is not suitable for an intraoperative procedure and cannot be tolerated by a nonnarcatosized patient.

2. The new stimulation method allows the method to be utilized with neurological or psychiatric illnesses in which the pathological rhythm are subject to strongly varying frequencies. Especially the new method can be used to desynchronize even intermittent (that is briefly arising) rhythms. The new stimulation method thus can be employed for a greater variety of illnesses, above all even in the case of epilepsy.

With the device according to the invention with the new stimulation method, the following illnesses or symptoms can be alleviated by the desynchronization of suitable framed areas. In all neurological and psychiatric illnesses in which pathologically synchronized neuronal activity plays a roll for the expression of the illness specific symptom, for example, parkinsonism, essential tremor, dystony, obsessive disorders, tremor in the case of multiple scolisis, tremor in the case of impact accident or the like, for example tumorus tissue damage, for example in the region of the thalamus and/or the basil ganglia, choreoathetosis and epilepsy, although this listing should not be considered as limiting.

By the standard measures used to date, the high frequency continuous stimulation, the following target areas are for example used:

In the case of parkinsonism, the nucleus subthalamicus or in the case of tremor dominant parkinsonism, the thalamus, for example, the nucleus ventralis intermetius thalami. In the case of essential tremor, the thalamus, for example, the nucleus ventralis intermetius thalami. In the case of dystony and choreoathetose the globus pallidum internum. With epilepsy, the nucleus subthalamicus, the seraberum, the thalamic nuclear region, for example the nucleus ventralis intermetius thalami or the nucleus caudatus. With obsessive disorder, the capsule interna or the nucleus accumbens.

With the device of the invention, by way of example, the target areas listed above for the respective illnesses can be selected. With the device of the invention, even no calibration is required or the calibration can be carried out more quickly. Thus providing the possibility of allowing alternative target areas to be tested during the electrode implantation so that the desynchronizing effect of the device of the invention can be more effective.

The invention also emcompasses a control which controls and carries out the required functions with the device according to the invention as well as the use of the device and the control for the treatment of parkinsonism, essential tremor, dystony, obsessive disorder, choreoathetose, tremor with multiple scolisis, tremor in the case of impact injuries or another, for example, tumorus tissue damage for example in the region of the thalamus and/or the basalganglien, and epilepsy.

The device of the invention can be used as an implant for continuous therapy of the above mentioned neurological and psychiatric illnesses as well as for the intraoperative target point diagnostic, that is the intraoperative determination of the optical target point for the electrode implantation.

The invention claimed is:

1. A method for desynchronizing neuronal brain activity of a patient in which the brain activity involves a neuron population firing in a synchronized manner, the method comprising:
    measuring a pathological frequency g of the neuronal brain activity of the patient, where the pathological frequency g relates to a pathological disorder of the patient;
    calculating a stimuli frequency f based on the measured pathological frequency g, wherein the calculated stimuli frequency f is calculated using the measured pathological frequency g×n/m, where n is 1, 2 or 3 and m is 1, 2 or 3; and
    controlling a stimulation unit to generate and deliver stimuli to an electrode in sequence with the stimuli succeeding each other at the stimuli frequency f, where the stimuli stimulate the neuron population of the patient.

2. The method of claim 1, further comprising controlling the stimulation unit to generate and deliver the stimuli to the electrode as bursts of electrical pulses.

3. The method of claim 2, further comprising varying when the electrical pulses in the bursts are applied either stochastically and/or deterministically.

4. The method of claim 1, further comprising controlling the stimulation unit to periodically generate and deliver the stimuli to the electrode.

5. The method of claim 1, further comprising controlling the stimulation unit to generate and deliver the stimuli to the electrode stochastically and/or deterministically.

6. The method of claim 1, further comprising controlling the stimulation unit to generate and deliver the stimuli to a further electrode, wherein the stimuli are delivered to the electrode and the further electrode in sequence and the stimuli applied to the further electrode succeed each other at the predetermined frequency.

7. The method of claim 6, further comprising controlling the stimulation unit to simultaneously generate and deliver the stimuli to the electrode and to the further electrode with different polarities.

8. The method of claim 6, further comprising controlling the stimulation unit to generate and deliver the stimuli to the electrode and to the further electrode, respectively, with a predetermined time shift and the same polarities.

9. The method of claim 6, further comprising controlling the stimulation unit to generate and deliver identical stimuli to the electrode and to the further electrode.

* * * * *